United States Patent [19]
Lemelson

[11] Patent Number: 5,871,774
[45] Date of Patent: Feb. 16, 1999

[54] DRUG UNITS AND METHODS FOR USE

[76] Inventor: Jerome H. Lemelson, Suite 286, Unit 802 930 Tahoe Blvd., Incline Village, Nev. 89451

[21] Appl. No.: 145,324

[22] Filed: Oct. 28, 1993

Related U.S. Application Data

[63] Continuation of Ser. No. 791,783, Nov. 12, 1991, Pat. No. 5,260,071, which is a continuation-in-part of Ser. No. 461,838, Dec. 18, 1989, abandoned.

[51] Int. Cl.$^6$ ................ A61K 9/16; A61K 9/50; A61K 9/54; A61K 9/62
[52] U.S. Cl. .............. 424/490; 424/452; 424/457; 424/458; 424/461; 424/463; 424/489; 424/493; 514/925; 514/926; 514/927
[58] Field of Search ................ 424/457, 463, 424/468, 476, 482, 490, 497, 498, 451, 464, 489, 452, 458, 461, 493

[56] References Cited

U.S. PATENT DOCUMENTS 5,202,311  4/1993  Folkman et al. .................. 514/12

FOREIGN PATENT DOCUMENTS 8300435  2/1983  United Kingdom .

*Primary Examiner*—Thurman K. Page
*Assistant Examiner*—James M. Spear

[57] ABSTRACT

Medical materials for use in treating maladies in living beings, such as ulcers and other conditions of the digestive tract. In one form, a container is provided for a medication which container also contains an adhesive material which is operatively released from the container or exposed at the surface thereof upon biodegradation or dissolution of a protective coating or wall portion of the container under the effects of fluid in the digestive tract in which the container is exposed, such as by swallowing, to permit such adhesive to temporarily bond and retain the container at a select location in the digestive tract so that it may slowly release its contents thereafter to a select portion of the digestive tract. In another form, a multitude of microcapsules, each containing a small quantity of medication, is mixed with an adhesive material, such as a sulcralfate other material which may be swallowed as a tablet or dissolved in a liquid such as water. Such microcapsules are carried with the adhesive material to be bonded temporarily therewith to a select portion of the wall of the digestive tract such that, upon biodegradation or dissolution of the walls of the capsules, the contents thereof may be released over an extended period of time to cooperate with the adhesive material in protecting the lining of the digestive tract from acids secreted by the body, food roughage and the like.

10 Claims, 2 Drawing Sheets

DRUG UNITS AND METHODS FOR USE

This is a continuation of application Ser. No. 07/791,783 filed on Nov. 12, 1991 U.S. Pat. No. 5,260,071, which is a continuation-in-part of application Ser. No. 461,838 filed on Dec. 18, 1989, now abandoned.

SUMMARY OF THE INVENTION

This invention relates to improvements in medical materials adapted to be ingested by swallowing and to retain their integrity until they reach select locations in the digestive track, such as a location in the small intestine or the large intestine where they operate to treat or cure a disease or malady, such as an ulcer, fistula or the like or to prevent the spread or degrading of same. While in a preferred form of the invention, the medical material is employed to coat and protect a select portion of the lower intestine from erosive or chemical or biological attack, such as effected by sucralfate which temporarily binds to the intestinal wall upon its release therein, other forms of the invention are operable to treat such intestinal maladies and protect the diseased or wound portions from the degenerative effects of body fluids and food.

In the preferred form of the invention, a quantity of a sucralfate formed of particles of a-D-Glucopyranoside, B-D-fructo-furanosyl-, octakis-(hydrogen sulfate), aluminum complex manufactured by Marion Laboratories, Inc. of Kansas City, Mo., is pressed into a tablet about one to two grams in weight and is coated with a biodegradeable or dissolvable coating which retains the integrity of the tablet until it reaches a select location of the lower intestine after which the coating degrades or dissolves allowing intestinal fluid to penetrate and cause release of the contents as a paste-like material which coats the intestine at and below the point of release. One or more additional treatment drugs mixed with the sucralfate or in microcapsules mixed in the tablet may also be provided to treat the wound(s) or diseased section of the intestine or cure same while the coating material protects the intestinal wall.

Accordingly it is a primary object of this invention to provide a new and improved method for medically protecting and treating diseases of the intestinal tract and drug units for effecting such treatment.

Another object is to provide a method for treating colitis of the lower intestinal tract by means of a protective medical agent which is ingested by mouth as a tablet or capsule and which remains intact until it reaches or approaches the lower intestine and thereafter releases its contents.

Another object is to provide a method for treating colitis of the lower intestinal tract with a material released from encapsulation in that portion of the intestinal tract containing ulcers or inflammation.

Another object is to provide a method and drug units for treating diseases of the lower intestine, which drug units are ingested by mouth and remain intact as they travel through the digestive tract, until they reach a select portion of the intestine located either just before or at a section or sections thereof containing a disease, such as ulcers or colitis condition, whereupon they release their medication which coats or otherwise treats the disease condition to the exclusion of other portions of the digestive tract.

Another object is to provide drug units and methods for treating diseases, deficiencies and injuries to the intestinal tract by the combined action of a coating and protecting material, such as a sucralfate, and a drug operable to heal reduce or eliminate diseased or ulcerated conditions.

Another object is to provide improved time released drug units or mixtures operable to treat stomach and intestinal disease conditions and means for delivering same to such organs without affecting the organ or organs leading thereto.

With the above and such other objects in view as may hereinafter more fully appear, the invention consists of the novel constructions, combinations and arrangements of parts as will be more fully described and illustrated in the accompanying drawings, but it is to be understood that changes, variations and modifications may be resorted to which fall within the scope of the invention as claimed.

BRIEF DESCRIPTION OF THE DRAWINGS

In the drawings:

In FIG. 1 is shown a first form of the invention in the form of a drug unit defining capsule or tablet 10 adapted to be swallowed by a person. The core 11 of the drug unit 10 is formed of a compressed amount of sucralfate provided as a solid oblong shape 12 having rounded or semi-spherical end portions 13 and 14, The mass of core 11 is formed of compressed particles of a normally dry material which easily and rapidly absorbs liquids and becomes adhesive, upon subjecting same to liquid material such as water or fluid of the digestive tract, to permit such material to temporarily adhere to surfaces, such as the lining of the digestive tract. Compressed particles of sucralfate may form the mass. Such material is formed of alpha-D-Glucopyrano-side, B-D-Fructofuranosyl-,octakis[Hydrogen Sulphate], aluminum complex. One such form of such material is manufactured as a tablet by Marion Lab. Inc., Kansas City, Mo. 64137 under the name of Carafate, the tablets of which weigh about one gram, and is utilized to treat ulcers and inflammation of the lower esophagus and stomach by coating same after the tablet disintegrates under the effect of saliva and stomach fluids or after such tablet is placed in a small quantity of water to effect such disintegration, which water and tablet mixture is swallowed by a patient. The result is a sucralfate-albumin film coated on the esophagus and stomach walls, which inhibit certain gastric juice activity and coats ulcers or inflamed areas thereof protecting same against mechanical and chemical attrition.

Surrounding and coating the entire outer surface 12S of core 11 including center portion 11C and end portions 13 and 14 thereof, is a thin layer 15 of a dissolvable material, such as a polymer, which dissolves in water or body fluid, the thickness and chemical-physical characteristics of which coating are such that it will remain surrounding the core 11 and prevent intestinal fluids from passing to the material of the core as the capsule travels the digestive tract until it reaches a select portion thereof, such as that portion of the large intestine which is ulcerated or inflamed with colitis or other condition requiring protection from body fluids and/or digested food products passing therethrough. At such select digestive tract portion, a portion or portions of the coating is completely removed by dissolution, erosion or biodegradation such that intestinal fluid passes to and is absorbed by the material of the core 11 allowing such material to expand break up and flow with body fluid in a manner to pass close to and contact a select portion or portions of the intestinal wall and to form a coating which adheres thereto for a period of time during which it is temporarily adhered to the the intestinal wall and protects same against physical attrition and the effects of intestinal fluid and bacteria.

If layer or coating 15 is of non-uniform thickness, a select thin portion thereof may dissolve or degrade before the main portion allowing the capsule to remain in tact and continue its travel down the intestine while its contents slowly flow therefrom to beneficially affect and coat an extending portion of the intestinal wall.

Figure 2:
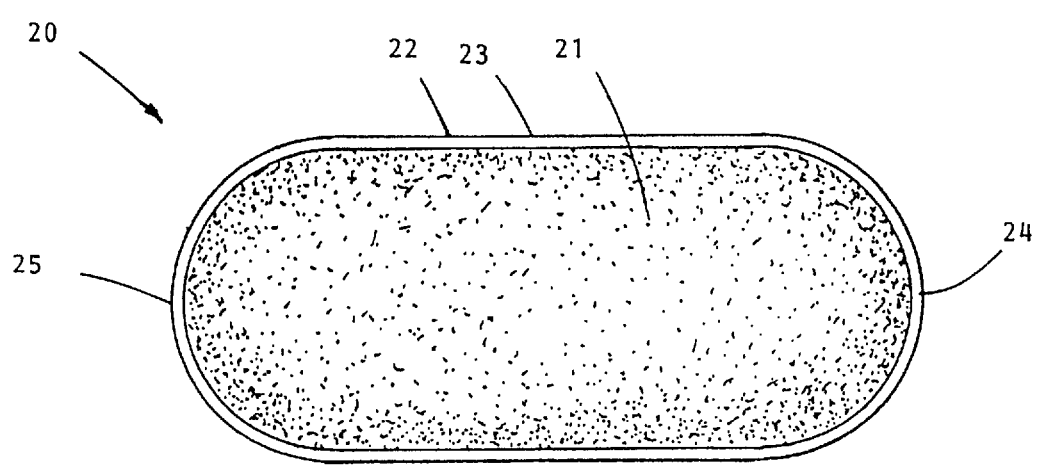
FIG. 2 is a side view of another form of the invention in the configuration of a capsule having a powdered core.

In FIG. 2 is shown a modified form of capsule 20 having a biodegradeable or dissolvable coating or preformed shell 22 formed with a cylindrical or oblong center portion 23 and rounded end portions 24, 25 and made of biodegradeable material such as a polymer, copolymer,starch or the like as described hereafter. Completely filling the shell 22 are loose particles 21 of a solid material, such as sucralfate which may rapidly absorb and become mixed with intestinal fluid when all or part of the material of the shell dissolves or biodegrades at a select location in the upper or lower intestine, as described above.

Figure 3:
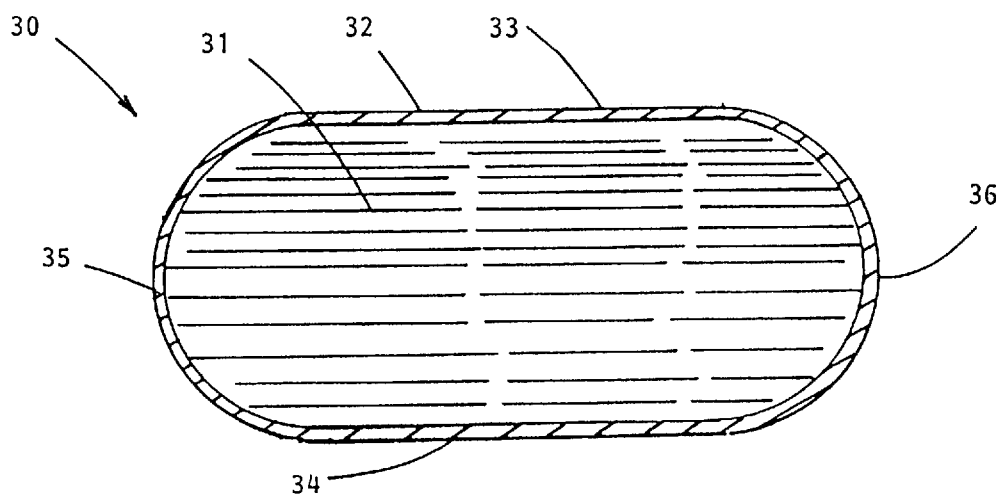
FIG. 3 is a side view of yet another form of the invention in the configuration of a capsule having a liquid filling its interior.

In a third form of the invention shown in FIG. 3 a swallowable drug unit 30 is provided defined by an oblong shell or capsule 32 made of gelatin or other suitable solid biodegradeable material, the wall 33 of which is of a thickness such that the capsule will dissolve or degrade under the effects of digestive tract fluid to a degree such that the contents thereof will be released when the drug unit reaches a select portion of the upper or lower intestinal tract. Filling the interior of the capsule 32 is a liquid 31 which may serve to coat and/or treat a disease, such as colitis or other malady existing at or near the location of the digestive tract where such liquid is released from the capsule.

The capsule 32 has a side wall 33 with a central portion 34 of substantially cylindrical shape and semi-spherically shaped end wall portions 35 and 36. The wall 33 may be of constant thickness along the side and/or end wall portions or may vary in thickness with one or more thinner portions thereof adapted to dissolve or degrade before the entire capsule degrades to permit the liquid contents to slowly flow therefrom as the capsule travels a distance along the intestine.

Figure 1:
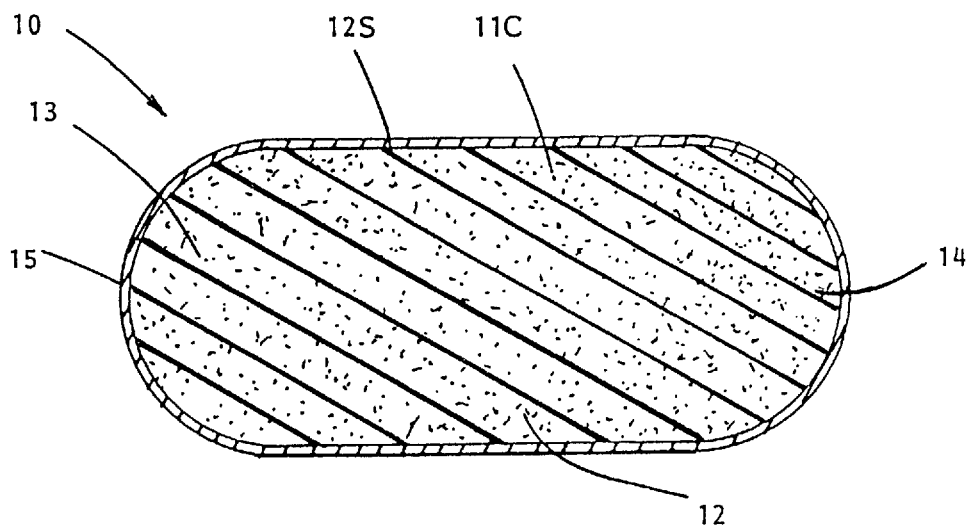
FIG. 1 is a side cross sectional view of a first form of drug unit in the configuration of a swallowable capsule or tablet having a solid core.

In the embodiments of the invention illustrated in FIGS. 1 to 3, it is noted that the active contents of the capsules or tablets may comprise a coating material, such as a sucralfate or other material or in combination therewith as a mixture or disposed as one or more subcapsules or solid units to be dispensed from the main capsule when it dissolves or biodegrades at a select location or locations of the intestine, for the purpose of treating and curing or reducing the malady being treated.

Where a second drug or a number of drugs are disposed in microcapsules disposed in the sucralfate materials of FIGS. 1 and 2, they may be temporarily adhesively bonded to and be retained against a select portion of the intestinal wall while they biodegrade and release their contents to treat such portion of the intestine to which they are so bonded.

In the forms of the invention illustrated in the drawings and described above, which utilize an intestinal fluid dissolvable coating or capsule, it is noted that the dissolving characteristics thereof and the thicknesses of the capsules are such that suitable partial or complete dissolution to start and effect release of the contained medication, is a function not only of such dissolving characteristics but also of the thickness of the coating or capsule. Accordingly, in one form of the invention, the coatings or capsule walls may be of constant thickness to provide substantially simultaneous release or access of intestinal tract fluid to the contents of the drug units. In another form, the thickness of the coating or containing capsule may vary along its length such that one or more portions thereof may dissolve and initiate the release of contents or admission of intestinal tract fluid to the interior of the container or drug unit prior to the dissolution and release or admission of other portions of the container or coating so as to effect a delay or delays in the release of the entire contents to provide such medication for treatment purposes over an extended period of time and along an extended portion of the digestive tract beyond that portion in which initial release is effected.

A number of groups of polymers may be applied to form the capsules described or the coatings on the tablets and may be coated or formed in thicknesses such as to effect release of their contents at a select location of the digestive tract upon dissolution or biodegradation. Such polymers as hydrogels, polyvinyl pyrrolidone, poly(vinyl) alcohol, ethylene-vinyl acetate copolymer, copolymer of hydroxyethyl methacrylate,etc. as well as certain natural waxes may also be employed for the coatings and capsules described in wall thicknesses which will effect their degradation or dissolution at the desired location of the upper or lower intestine.

Other forms of the invention are noted as follows:

1. The described drug unit or units which release their contents after being swallowed and allowed to travel down the digestive tract, may contain a quantity or quantities of a healing substance, such as the healing protein epidermal growth factor (EGF) or other medication useful in treating and/or healing disease conditions of the stomach, upper or lower intestine where release thereof from encapsulation is effected as described herein. Such epidermal growth factor may be provided in dry powdered form as the sole contents of the dissolvable or biodegradeable capsule or microcapsules therein or a mixture of same with the described sucralfate to be released therewith to the intestine. The released mixture may serve to coat a select area of the intestinal wall adjacent and below the location at which release is effected and to treat one or more wounds, fistulas or ulcers therein with the growth factor which may serve one or both of two purposes. A first of the functions of the growth factor is to effect and accelerate healing of the ulcer(s) or wound(s). A second is to effect or accelerate the growth of new tissue at the wound and/or along that portion of the intestinal lining where the medication is released and/or held against the lining as the medication per se and/or microcapsules containing same.

2. A multitude of body fluid dissolvable microcapsules containing a suitable medication, such as epidermal growth factor or other medication for treating a condition of the intestinal tract or stomach, may be mixed with a temporary adhesive material, such as sucralfate which mixture is pressed into tablet form and coated with dissolvable material as described or made to fill a dissolvable capsule to be released therefrom at a select location in the upper or lower intestine for retention and release as described, after ingestion by mouth or placement by a tool at a select location. Biodegradeable adhesives other than sucralfate such as natural or synthetic liquid adhesives, may be mixed with the microcapsules or disposed therein for release therefrom at a select location or locations of the digestive tract as described.

3. If the drug unit contains a coating material or a medication which is not sufficiently adhesive to retain it against that portion of the wall of the intestinal tract adjacent which it is released from encapsulation, a suitable biodegradeable adhesive material may be mixed with same or coated on the microcapsules containing same within the main container to serve to bond such coating material or microcapsules of drug to the portion of the intestinal wall against which it is disposed upon release from the main container. In other words, the adhesive may be disposed within the main container mixed with the particulate coating material, coating the microspheres of medication therein and/or contained within such microspheres or microcontainers.

4. In yet another embodiment, the drug and/or coating material contained within the main container may be released therefrom by means other than by biodegradation or dissolution of the wall of the container. The main container may be operable to pass completely through the intestinal tract without degrading and may contain a valve operated by a miniature actuator, motor or solenoid to open and release all or part of the drug and/or coating contents of the container in response to a short wave signal, radiation such as microwave radiation, ultrasonic signal or magnetic field applied by suitable instrumentation and generating means located exterior of the body such as aligned with that portion of the intestinal tract containing the disease or ulcer condition.

Where employed herein and in the claims, the term "biodegradable" or "biodegradation" refers to processes whereby body fluid, such as intestinal fluid and fluid of the stomach serves to either degrade by biological action and/or dissolve an encapsulating material or coating surrounding a drug unit or small quantity of drug.

5. In yet another form of the invention, the containers of FIGS. 1–3 may each contain a small permanent magnet which is operable to hold the container at a select location of the intestinal tract under the attraction force of another magnet, such as a permanent or electromagnet disposed against a select portion of the skin aligned with the abdominal wall adjacent said select portion of intestine. Release of the drug or medical coating material contents of the magnetically held container or drug unit may be effected thereafter by one or more means, such as biodegradation or dissolution of a portion, portions or the entire wall of the main container or by the operation of a valve in or aligned with an opening or openings in the container wall. Such valve or valves in the container may be opened from a closed condition by magnetic force or radiation, such as a short wave energy field applied from the exterior of the body to suitable receiving and valve actuating means. After the drug contents of the container have received body fluid to condition same for release or have completely or partly flowed from the container past such valve, the container may be released from its magnetically held position by removal of the magnetic field from its vicinity, and may travel down the intestine to the next location where its contents are required to be released in a similar manner or excreted from the intestine thereafter.

6. In the treatment of diseases of the lower digestive tract, such as ulcerated colitis, a substantially greater amount of the drug or drug mixture released when the encapsulation means therefor degrades or dissolves will contact and coat the wall of the lower intestine if the waste or feces in the lower intestine is rendered in a loose or highly fluid state. Such condition may be effected during treatment by ingesting and swallowing a suitable cathartic prior to injesting the drug unit described or including such a cathartic in the drug unit. If the stools formed in the lower intestine are kept highly fluid or liquid by ingesting one or more doses of a cathartic or laxative, release of the drug contents of the drug unit while in and/or just prior to the entry of the drug unit into the large intestine will permit the contents thereof to flow to and contact a substantially larger portion of the wall of the intestine than if the waste matter is solid or less fluid. For certain treatment procedures, the taking of a suitable dose of a cathartic by mouth and the inclusion of a cathartic with the medication of the drug unit will be necessary to effect suitable treatment as described.

In yet another form of treatment procedure involving drug units as described above, several liters of a solution of water and the salts of sodium chloride, sodium bicarbonate and potassium chloride taken by mouth over a period of several hours will result in clearing the lower intestine of solid matter. If one or more of such drug containing pills or capsules are taken during or after the drinking of the latter amount of such a solution as defined by the medication NuLYTELY (marketed by Braintree Laboratories of Braintree, Mass.) and each drug unit is operable to release its contents at a select portion of the large intestine, then a maximum amount of the described medication or medications contained thereby will contact, coat and react on the tissue of the wall of the large or lower intestine as desribed above. Similarly, if it is required to coat and treat an ulcer or ulcers in the wall of the stomach or duodenum with an epidermal growth factor as described to aid and accelerate healing of the ulcer or ulcers, each drug unit may be taken between meals with a liquid such as water to assure its dissolution in the stomach or duodenum and its contacting the wound tissue or ulcer with the epidermal growth factor with or without the sucralfate or other surface coating medical material or bioadhesive.

Thus it is seen that in additional to the encapsulating coating or container, the contents thereof may comprise one or more of the following: (a) a surface coating medical material such as a sucralfrate, (b) an epidermal growth factor, such as a quantity of a biologically engineered and grown growth factor such as G-CSF, GM-CSF or erythropoietin which promote the growth of select digestive tract cells such as the cells of a wound or ulcer in the intestine, stomach or duodenum and (c) a laxative or cathartic if treatment is to be effected of tissue of the lower or large intestine.

7. To help fight infection and further promote healing of an internal wound or ulcer, a quantity of the growth factor M-CSF may also be included in the drug unit to stimulate the production of interlukins 1 and 3 and macrophages.

8. If the digestive tract wound is bleeding, such as if the wound is a bleeding ulcer, a quantity of the growth factor PDGF which promotes blood clotting, may also be included in the drug unit to be released in the general area of the wound and to cooperate with the one or more other medications described in promoting and effecting healing of such wound or wounds.

9. Two or more growth factors, such as one or more promoting select tissue growth (erythropoietin), another such as G-CSF to promote reproduction of granulocytes and macrophages, one or more such as M-CSF to promote the growth of interlukins and macrophages or platelet derived growth factor (PDGF), may be included in the simple drug unit capsule or tablet to cooperate in treating select wounds or wound tissue of the wall of the digestive tract when delivered, as described, to s select portion or portions of the stomach, duodenum, upper or lower digestive tract.

What is claimed is:

1. A method for treating ulcerative disease of the intestinal tract comprising:
   a) forming an ulcer medication wherein said medication includes an antibiotic, and combining said medication with a select quantity of sucralfate in the form of an ingestable drug unit;
   b) orally administering to a patient said drug unit so that said medication and sucralfate reaches the diseased portion of the intestinal tract;
   c) allowing the sucralfate to contact and become adhered to ulcerated tissue of the wall of the digestive tract; and
   d) allowing said medication combined with the sucralfate to diffuse therefrom and act on the ulcerated tissue to which the sucralfate is adhered.

2. A method in accordance with claim 1 wherein said ulcer medication includes a biologically engineered growth factor.

3. A method in accordance with claim 1 wherein said ulcer medication is in the form of biodegradeable microcapsules.

4. A composition for treating ulcers of the intestinal tract comprising sucralfate combined with an ulcer medication in the form of an ingestable drug unit, wherein said ulcer medication is an antibiotic.

5. A composition in accordance with claim 4 wherein said ulcer medication includes a biologically engineered growth factor.

6. A composition in accordance with claim 4 wherein said ulcer medication is in the form of biodegradeable microcapsules.

7. A composition in accordance with claim 4 further comprising a biodegradeable coating material designed to dissolve in a select portion of the intestinal tract.

8. A composition in accordance with claim 4 further comprising a growth factor.

9. A composition in accordance with claim 8 wherein said ulcer medication is in the form of biodegradeable microcapsules.

10. A composition in accordance with claim 8 further comprising a biodegradeable coating material designed to dissolve in a select portion of the intestinal tract.

* * * * *